(12) United States Patent
Moritz et al.

(10) Patent No.: US 7,041,199 B1
(45) Date of Patent: May 9, 2006

(54) PROCESS AND DEVICE FOR HYDROLYTICALLY OBTAINING A CARBOXYLIC ACID ALCOHOL FROM THE CORRESPONDING CARBOXYLATE

(75) Inventors: Peter Moritz, Winterthur (CH); Franz Ramgraber, Burghausen (DE); Claudia von Scala, Zurich (CH); Harald Michl, Kastl (DE)

(73) Assignees: Sulzer Chemtech AG, Winterthur (CH); Wacker Chemie GmbH, Munich (DE)

( * ) Notice: Subject to any disclaimer, the term of this patent is extended or adjusted under 35 U.S.C. 154(b) by 641 days.

(21) Appl. No.: 10/110,474

(22) PCT Filed: Oct. 11, 2000

(86) PCT No.: PCT/CH00/00551

§ 371 (c)(1),
(2), (4) Date: Apr. 12, 2002

(87) PCT Pub. No.: WO01/27062

PCT Pub. Date: Apr. 19, 2001

(30) Foreign Application Priority Data

Oct. 13, 1999 (CH) .................. 1869/99

(51) Int. Cl.
*B01D 3/00* (2006.01)
*C07C 51/09* (2006.01)
*C07C 51/44* (2006.01)

(52) U.S. Cl. .............. 203/29; 202/154; 202/155; 202/158; 203/43; 203/71; 203/DIG. 6; 562/483; 562/608; 568/877; 568/913

(58) Field of Classification Search ............ 203/29, 203/43, DIG. 6, 71, DIG. 23; 202/154, 155, 202/158; 422/190; 568/877, 913; 562/608, 562/483

See application file for complete search history.

(56) References Cited

U.S. PATENT DOCUMENTS

| | | | |
|---|---|---|---|
| 3,972,912 A | 8/1976 | Wulf et al. | |
| 4,034,005 A | 7/1977 | Hancock et al. | |
| 4,352,940 A | 10/1982 | Adelman et al. | |
| 4,481,146 A * | 11/1984 | Leupold et al. | 554/170 |
| 4,569,725 A * | 2/1986 | Lindner et al. | 203/38 |
| 4,927,954 A * | 5/1990 | Knopf et al. | 558/441 |
| 5,113,015 A * | 5/1992 | Palmer et al. | 562/608 |
| 5,248,836 A | 9/1993 | Bakshi et al. | |
| 5,523,061 A * | 6/1996 | Hao et al. | 422/191 |
| 5,612,007 A * | 3/1997 | Abrams | 422/189 |
| 5,637,777 A * | 6/1997 | Aittamaa et al. | 568/697 |
| 5,705,711 A | 1/1998 | Preston | |
| 5,770,770 A | 6/1998 | Kim et al. | |
| 6,657,090 B1 * | 12/2003 | Rix et al. | 568/697 |
| 2002/0077501 A1 * | 6/2002 | Hoyme et al. | 562/512 |

* cited by examiner

Primary Examiner—Virginia Manoharan
(74) Attorney, Agent, or Firm—Buchanan Ingersoll PC (57) ABSTRACT

A process and a device for the catalytic hydrolysis of a carboxylate, e.g., methyl acetate, ethyl acetate, i- or n-propyl acetate, i- or n-butyl acetate, allyl acetate and methyl formate, into the corresponding carboxylic acid and alcohol, by a combination of a pre-reactor and a reactive distillation column are disclosed. By the combination of a pre-reactor and a reactor distillation column, the conversion ratio can be substantially improved. The device can compensate for fluctuations in the supply quantity or in the composition of the feed flow. The product composition can also be controlled in a wide range.

31 Claims, 5 Drawing Sheets

PROCESS AND DEVICE FOR HYDROLYTICALLY OBTAINING A CARBOXYLIC ACID ALCOHOL FROM THE CORRESPONDING CARBOXYLATE

TECHNICAL FIELD

The present invention relates to a process and to a device for the simultaneous hydrolytic cleavage of a carboxylate into the corresponding carboxylic and alcohol.

BACKGROUND OF THE INVENTION

Carboxylates, especially low molecular weight carboxylates, occur in the chemical industry during various reactions as by-products or main products. For example, methyl acetate is a typical by-product in the production of purified polyvinyl alcohol. Methyl acetate mixtures from polyvinyl alcohol plants, besides a small amount of low-boiling substances such as acetaldehyde, contain an azeotropic mixture of methyl acetate and methanol.

For chemical companies, where methyl acetate as a by-product occurs in relatively small quantities, methyl acetate is not an economically interesting product, since it cannot be profitably sold on the market. A better price can be obtained if methyl acetate is hydrolysed into acetic acid and methanol. The hydrolysis can be carried out either as a batch process or continuously, by using either a reactor in conjunction with conventional distillation or a single reactive distillation column.

The use of a reactor in conjunction with a distillation column for the hydrolysis of methyl acetate is described, for example, in U.S. Pat. No. 4,352,940. This type of hydrolysis of methyl acetate has several disadvantages: (a) since the reaction is an equilibrium reaction with a small equilibrium constant, the yield of reaction product is small, (b) because of the azeotropic mixture which is set up in the reaction mixture between methyl acetate/water, on the one hand, and methyl acetate/methanol, on the other, several distillation stages are needed after the reaction. This leads to high investment and running costs, (c) corrosion problems occur because homogeneous catalysts such as sulphuric and hydrochloric acid are used in the known conventional processes.

U.S. Pat. No. 5,113,015 discloses a process for obtaining acetic acid from methyl acetate, in which methyl acetate and water are brought into contact in the presence of catalyst packing in a distillation column. In this case, the methyl acetate is hydrolysed into acetic acid and methanol. The resulting reaction mixture is in this case partially separated at the same time in the separation column.

U.S. Pat. No. 5,770,770 likewise discloses a process for the hydrolysis of a methyl acetate mixture in a reactive distillation column. The hydrolysis of a methyl acetate flow, which contains more than 50% methyl acetate, takes place in a reaction zone in which ion exchange packing is present. The methyl acetate mixture is supplied from below to the ion exchange packing, and water from above onto the ion exchange packing. The unreacted methyl acetate and water vapour are collected and condensed in the upper part of the reaction zone, and are then recycled back to the reaction zone. At the same time, the base is collected and separated into the hydrolysis products and impurities. The impurities are then returned to the reaction zone.

Both aforementioned U.S. patents, U.S. Pat. Nos. 5,113,015 and 5,770,770, teach the use of strongly acid ion exchangers as catalysts. In U.S. Pat. No. 5,770,770, it is proposed to put the ion exchange material in the form of Raschig rings, by adding a plastic as binder to the ion exchanger and pressing the mixture into appropriate shapes. In U.S. Pat. No. 5,113,015, the catalyst material is conserved in glass wool, and the mat formed therefrom is rolled up with a wire mesh between the layers, in order to promote circulation of the fluids. The catalyst packing material may be a compliant open-mesh substance, e.g. a metal cloth. Another usable material is a more rigid cellular monolith, which can be produced from steel, polymers or ceramic material. The catalyst packing material may, however, also be produced from corrugated metal sheets or corrugated plastic or ceramic plates.

The processes described above, which use only a single reactive distillation column, suffer from the fact that methyl acetate is only partially converted to methanol and acetic acid. The amount of methyl acetate in the product flow makes the use of at least one additional purification stage necessary, which leads to additional investment and running costs. A further problem is that the methyl acetate feed flow often contains metal ions, which poison the catalyst in the reactive distillation column. The replacement of the catalyst material in the distillation column by fresh material, however, is laborious and expensive. Furthermore, it is desirable for the hydrolysis process to be controlled independently of the methyl acetate concentration in the feed flow—in such a way that, as required by the operator e.g. of a polyvinyl alcohol plant, the acetic acid obtained has a specific water content or is virtually anhydrous.

The object of the present invention is therefore to provide an improved process for the hydrolysis of a carboxylate, especially methyl acetate, methyl formate and allyl acetate, by using a reactive distillation column. In particular, it is desirable to improve the conversion ratio of carboxylates into alcohol and carboxylic acid. A further object is to prevent poisoning of the catalyst used in the distillation column. Another object is to optimise the energy budget of the process. It is also intended to offer a process and a hydrolysis device, which allow great flexibility in terms of composition and quantity of the feed. The composition of the product flows is also intended to be controllable in a large range by the process. A further object is to improve the conversion ratio of methyl acetate into acetic acid and methanol.

DESCRIPTION

According to the invention, this is achieved in the case of a process in which the feed containing the carboxylate is firstly fed into a pre-reactor, in which the carboxylate is brought into contact with a first catalyst in the presence of water, by means of which the carboxylate is partially cleaved into the hydrolysis products. The reaction mixture from the pre-reactor is fed into the reactive distillation column, and is brought into contact with a second hydrolysis catalyst for at least partial conversion of the remaining carboxylate into the corresponding carboxylic acid and alcohol. The process according to the invention has the surprising advantage that a substantially higher conversion ratio can be achieved than with known processes. A further advantage is that, by the use of a pre-reactor, the working life of the reactive distillation column can be substantially lengthened, since catalyst poisons, e.g. metal ions, are predominantly trapped in the pre-reactor. A further advantage is that, by the pre-reactor, differences or fluctuations in the feed quantity or in the mixture composition can be compensated. Yet another advantage is that the particle size of the catalyst material used in the prereactor plays a less important role than in the case of the catalyst packings advantageously used in the reactive distillation column. Batches with a specific particle size are normally used for catalyst packings, since the catalyst material could not otherwise be fully retained by the partially permeable packing walls.

Advantageously, at least the head flow of the reactive distillation column or the base flow is delivered to at least one further separation stage, and is at least partially separated into the components. One or more downstream separation stages are preferably used if the resulting reaction mixture is to be separated as fully as possible into the individual components.

Advantageously, the carboxylate flow is mixed with at least an equimolar amount of water, and the carboxylate/water mixture is fed into the pre-reactor. The molar ratio between carboxylate and water is expediently between approximately 1:1 and 1:15, preferably between 1:2 and 1:10, and more particularly preferably between 1:4 and 1:7. The hydrolysis proceeds particularly well if the carboxylate/water ratio in the feed flow is between 1:3 and 1:5.

Although the hydrolysis reaction can actually be carried out at room temperature, the carboxylate/water mixture is preferably heated to a temperature of between 30 and 100° C., preferably from 40 to 90° C., and more particularly preferably between 50 and 80° C., since the reaction proceeds well and quickly at these temperatures. The reaction mixture from the pre-reactor is expediently fed into the reactive distillation column in the region either where the catalyst is arranged, or slightly above or below this region. The head flow containing alcohol, water, carboxylate and volatile components may be delivered to a further separation stage, preferably a distillation column, in which the mixture is further separated.

Particularly advantageously, the reactive distillation column is operated in such a way that the carboxylic acid and at least one part of the water remain in the base of the reactive distillation column. In this case, the reaction mixture from the pre-reactor is preferably introduced into the reactive distillation column at a point above the catalyst zone centre. The base flow produced, which essentially contains alcohol, water and carboxylic acid, may be delivered to a further separation stage, preferably a distillation column, in which the mixture is further separated. It is also conceivable for both the head flow and the base flow of the reactive distillation column to be delivered to further separation stages, e.g. distillation columns, and separated. As a variant, the head product may be delivered partially to the pre-reactor or to the feed flow of the reaction column, in order to further convert carboxylate contained in the head flow. Such recycling of the head flow of the reactive distillation column allows the capacity of the plant to be increased substantially.

Advantageously, the reactive distillation column is operated in such a way that the added water and the volatile components are essentially contained in the head flow. This has the advantage that the carboxylic acid is produced in the base with a proportion by weight >95%, preferably >99%. The highest conversion ratio can in this case be achieved if the reaction mixture from the pre-reactor is introduced into the reactive distillation column at a point below the catalyst zone centre.

The process according to the invention is advantageously operated continuously, i.e. carboxylate and water or a mixture thereof, respectively, are continuously fed into the pre-reactor, and the resulting reaction mixture is drawn off continuously from the pre-reactor and fed into the reactive distillation column, where unreacted carboxylate is for the most part converted into its hydrolysis products, the hydrolysis products being drawn off continuously as a head flow or as a bottom fraction (base flow), and optionally delivered to a further separation stage. The volume flow delivered per unit volume of catalyst is advantageously between $0-15\ h^{-1}$, preferably $0.5-8\ h^{-1}$ and particularly preferably between $1-4\ h^{-1}$.

The present invention also relates to a reaction and separation device, characterised by at least one pre-reactor having at least one inlet and one outlet for respectively supplying and discharging a fluid flow comprising the carboxylate or the carboxylate mixture into the pre-reactor and therefrom, respectively, a first catalyst, which is arranged or deposited in the pre-reactor, a connecting line, which connects the outlet of the pre-reactor to the inlet of the reactive distillation column, and first heating means for heating the fluid flow or the pre-reactor. The advantages of this device according to the invention have already been mentioned in connection with the description of the process. Advantageous refinements of the device are described herein.

As a result of the fact that the pre-reactor is arranged approximately vertical, and the inlet is located at the top and the outlet at the bottom, the catalyst material in the pre-reactor experiences vortexing, since the flow direction of the reaction flow and gravity keep the catalyst material at the bottom of the pre-reactor. It is thereby possible to prevent undesired attrition of the catalyst material. It is also conceivable for the inlet and outlet to be provided laterally on opposite sides above or below the catalyst zone, respectively. It is in principle also conceivable for the inlet to be arranged at the bottom and the outlet at the top.

In a particularly preferred embodiment, two pre-reactors or one pre-reactor having two reaction chambers are used, and means are provided for making it possible to send the feed flow respectively through one of the pre-reactors or one of the reaction chambers, so that the other pre-reactor or the other reaction chamber, respectively, can be provided with fresh catalyst. This has the advantage that the device can be operated continuously for a long period of time. It is also conceivable to arrange the two pre-reactors one behind the other. Such an arrangement has the advantage that different temperatures can be maintained in the two reactors, in order to positively exploit the dependency of the equilibrium reaction on temperature (e.g. 1st reactor is operated at a higher temperature than 2nd reactor). According to an advantageous processor variant, the flow leaving the pre-reactor may be partially returned to the pre-reactor. This has the advantage that the pre-reactor can be dimensioned smaller than if no recycling line is provided around the pre-reactor, and the capacity of the plant is variable in a larger range. Yet another advantage is that phase separation in the feed to the pre-reactor can be avoided by a recycled flow.

Expediently, the reactive distillation column has a catalyst zone and one lower and one upper rectification zone, the upper rectification zone being provided above the catalyst zone and the lower rectification zone being provided below the catalyst zone. The rectification zone may have separating stages, Raschig rings, structured material exchange packings etc.

The pre-reactor is advantageously designed as a tube, in which the first catalyst is deposited. Expediently, the first and second catalysts are acid solid-state catalysts, the first catalyst having a particle size of between approximately 0.35 and 3 mm and the second catalyst having one between approximately 0.5 and 1.5 mm, preferably 0.63 and 1 mm, and more particularly preferably between 0.7 and 1 mm. While the first catalyst is preferably present as a bed in the pre-reactor in the form of spheres, rings, extrudates etc., the second catalyst is advantageously introduced into the reactive distillation column as so-called structured catalyst packing. Suitable structured catalyst packings are described, for example, in U.S. Pat. No. 5,417,939 (Shelden), U.S. Pat. No. 5,470,542 (Stringaro) and U.S. Pat. No. 5,536,699 (Ghelfi), the content of which is hereby included by reference. The term structured catalyst packing should be understood to mean a structure having retaining devices (e.g. bags) for solid catalyst material and having flow channels, which are present in the structure. It is also conceivable to use such structured catalyst packings both in the pre-reactor and in the reactive distillation column.

Figure 1:
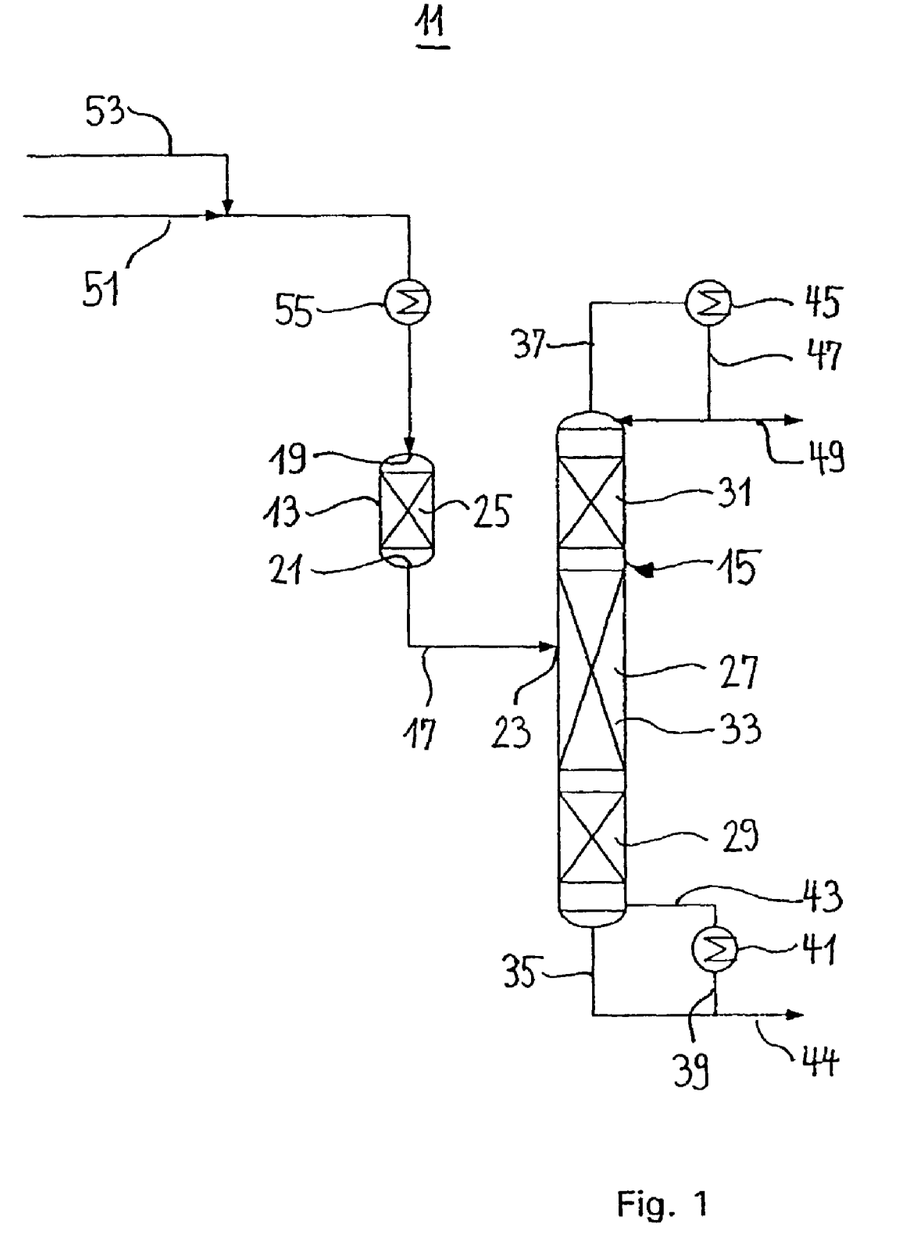
FIG. 1 diagrammatically shows a first embodiment of a device for the catalytic hydrolysis of carboxylates, with a pre-reactor and a reactive distillation column.

The device 11 for the simultaneous catalytic hydrolysis of a carboxylate, especially methyl acetate, methyl formate or allyl acetate, into the hydrolysis products and at least partial separation of the reaction mixture, comprises essentially a pre-reactor 13 and a reactive distillation column 15, which are connected to one another by a connecting line 17.

The pre-reactor 13 has an inlet 19 for feeding a fluid flow into the reactor space and an outlet 21 for drawing off the reaction mixture. The connecting line 17 connects the outlet 21 of the reactor to an inlet 23 on the reactive distillation column 15. The pre-reactor 13 is preferably tubular, the inlet 19 and the inlet [sic] 21 being arranged on opposite end sides of the tube. The pre-reactor 13 has a catalyst bed 25 of a solid first catalyst material.

The reactive distillation column 15 has a catalyst zone 27 and an upper and lower rectification zone 29, 31, which are provided respectively below and above the catalyst zone 27. A second solid-state catalyst 33, preferably contained in so-called catalyst packing, is provided in the catalyst zone 27. The rectification zones are formed in a known way e.g. by Raschig rings, column stages, structured (material exchange) packings etc. A line 35 for drawing off the base flow is provided at the column foot, and a line 37 for drawing off the head flow of the reactive distillation column 15 is provided at the column head. The line 35 is in connection by means of a line 39 with a heat exchanger 41, which is connected via a line 43 in turn to the column base. The heat exchanger 41 is used to heat the column base. By means of a branch line 44, part of the base can be removed as a base or base [sic] flow from the hydrolysis and separation device.

The line 37 for the head flow leads to a condenser 45, by which the gaseous head flow can be liquefied. By means of a recycling line 47 connected to the condenser, part of the distillate can be returned as recycle to the reactive distillation column 15. Part or all of the distillate from the reactive distillation column 15 can be removed via the line 49.

The carboxylate compound to be hydrolysed can be delivered into the pre-reactor 13 via a line 51, which is connected to the inlet 19. Water can be added to the line 51 via a line 53. The carboxylate/water mixture can be heated by a heat exchanger 55, which is in connection with the line 51.

The second illustrative embodiment (FIG. 2) differs from the first in that a distillation column 57 is connected to the line 44, which is in connection with the column foot. For the sake of simplifying the description, the same reference numbers as in the description of the first illustrative embodiment are therefore used for identical parts, and the description is limited to the additional features of the second illustrative embodiment.

Figure 2:
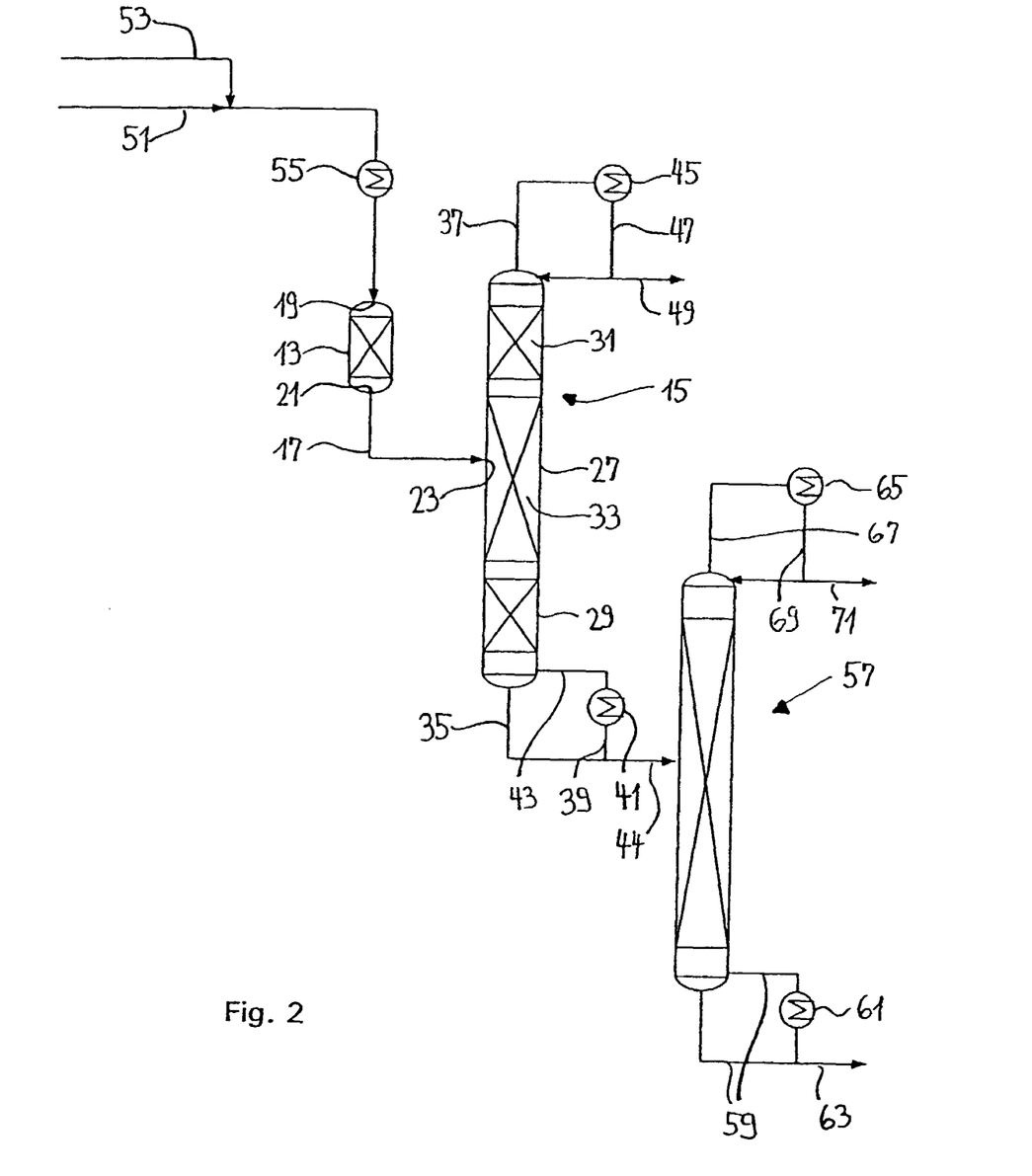
FIG. 2 diagrammatically shows a second embodiment of a device for the catalytic hydrolysis of carboxylates, with a pre-reactor, a reactive distillation column and a distillation column for further separation of the bottom fraction of the reactive distillation column.

Like the reactive distillation column 15, the distillation column 57 also has a heat exchanger 61, integrated in a circulation line 59, in order to heat the base of the distillation column 57. Part of the distillation base can be removed from the hydrolysis device by a branch line 63.

At the head of the distillation column 57, a condenser 65 is connected by means of a line 67 to the column. The condensate can be returned via the line 69 into the distillation column, or can be removed via the line 71 from the hydrolysis and separation device.

Figure 3:
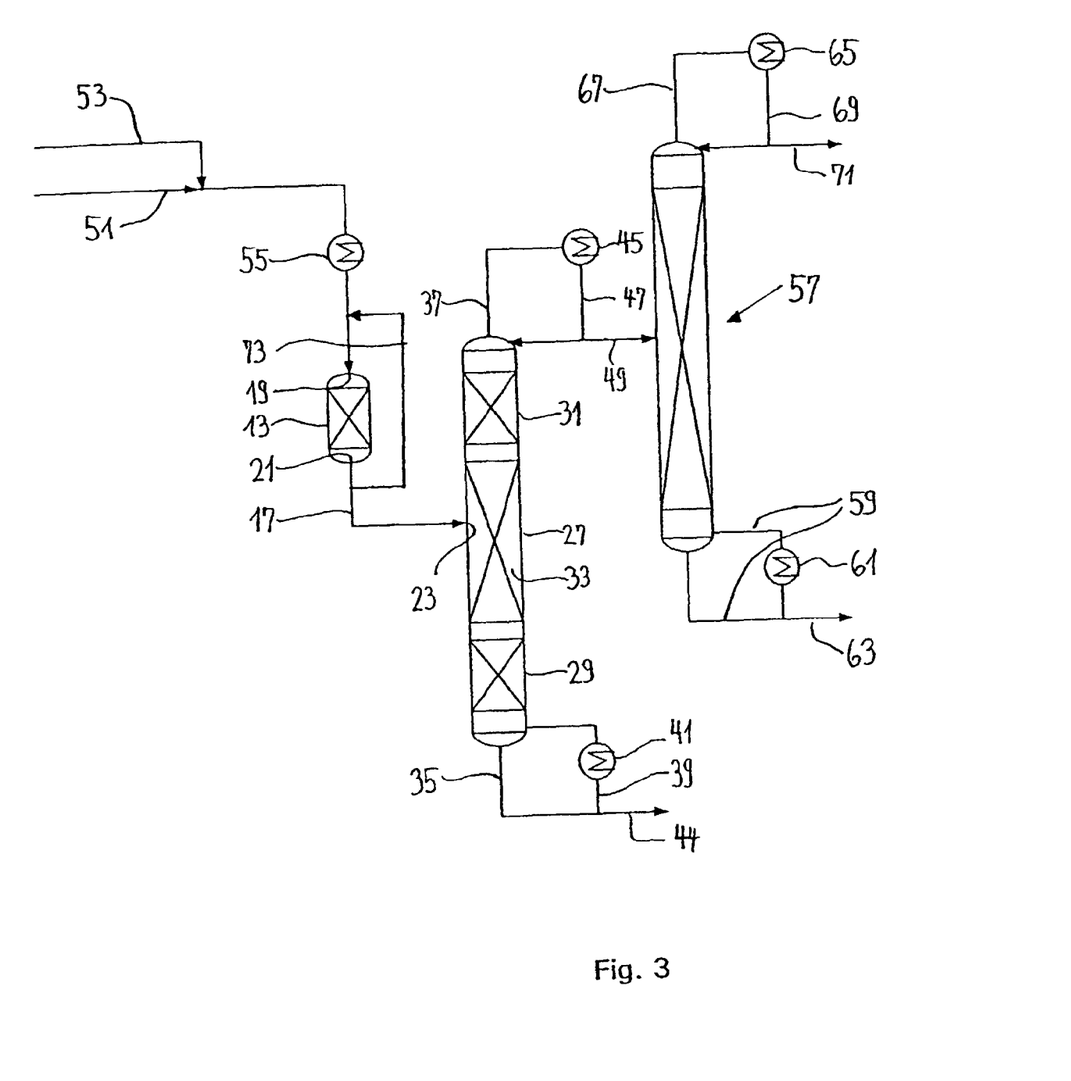
FIG. 3 diagrammatically shows a third embodiment of a device for the catalytic hydrolysis of carboxylates, with a pre-reactor, a reactive distillation column and a distillation column for further separation of the head flow of the reactive distillation column.

The illustrative embodiment in FIG. 3 differs from that in FIG. 2 in that the distillation column 57 is connected to the line 49, which is in connection with the condenser 45 of the reactive distillation column. By means of the distillation column, the head flow, which may be a compound mixture, can be separated at least partially into the components. A further difference is that a recycling or recirculation line 73 is provided around the pre-reactor 13, in order to make it possible for part of the flow leaving the pre-reactor 13 to be delivered newly thereto. Depending on the separation problem, an extraction column may also be used instead of the distillation column.

Figure 4:
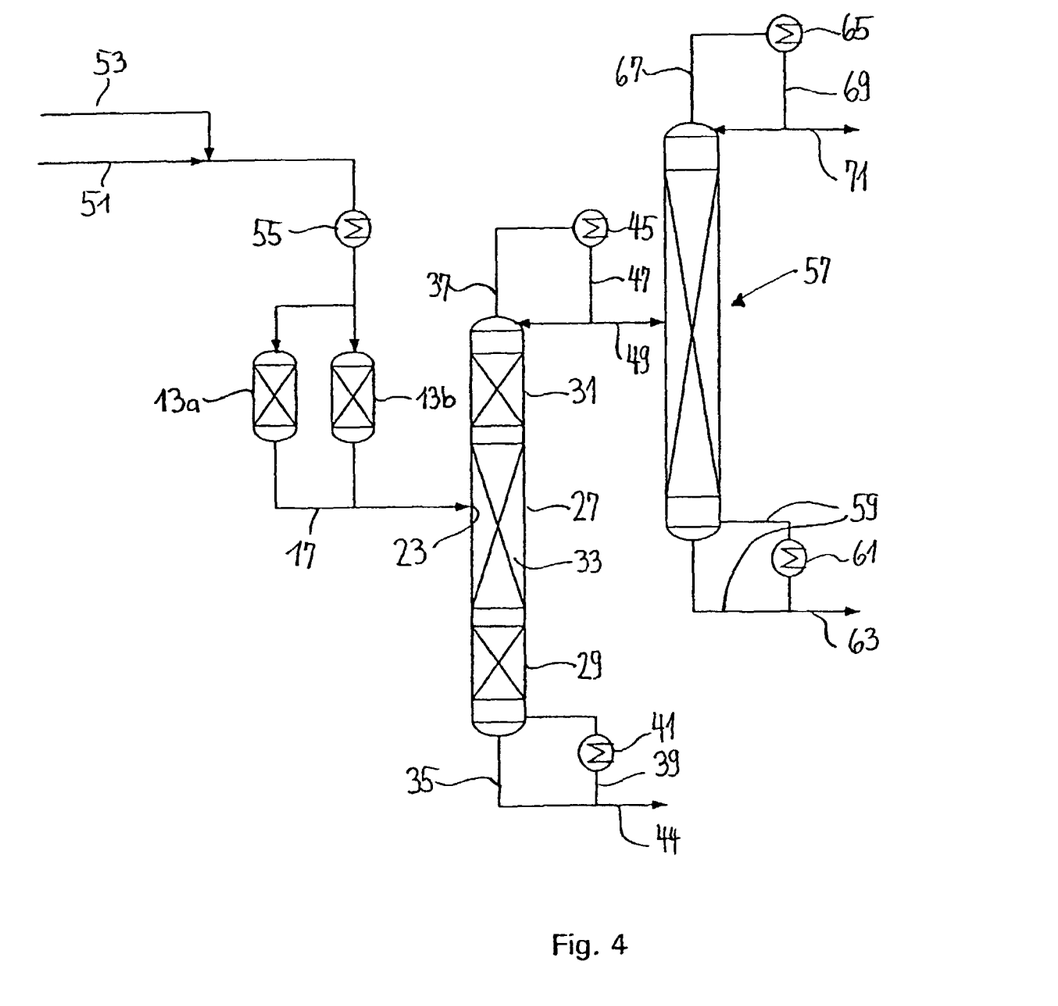
FIG. 4 diagrammatically shows a fourth embodiment of a device for the catalytic hydrolysis of carboxylates, with two pre-reactors.

The illustrative embodiment in FIG. 4 has the distinguishing feature of two pre-reactors 13a and 13b, which can be used simultaneously or alternately. The reaction flow can in this case be fed through valves (not represented in further detail) either through the pre-reactor 13a or pre-reactor 13b. The use of two pre-reactors has the advantage of that, in the event that it is necessary to replace the catalyst material in one pre-reactor, operation need not be interrupted since the process flow can be fed through the other pre-reactor.

Figure 5:
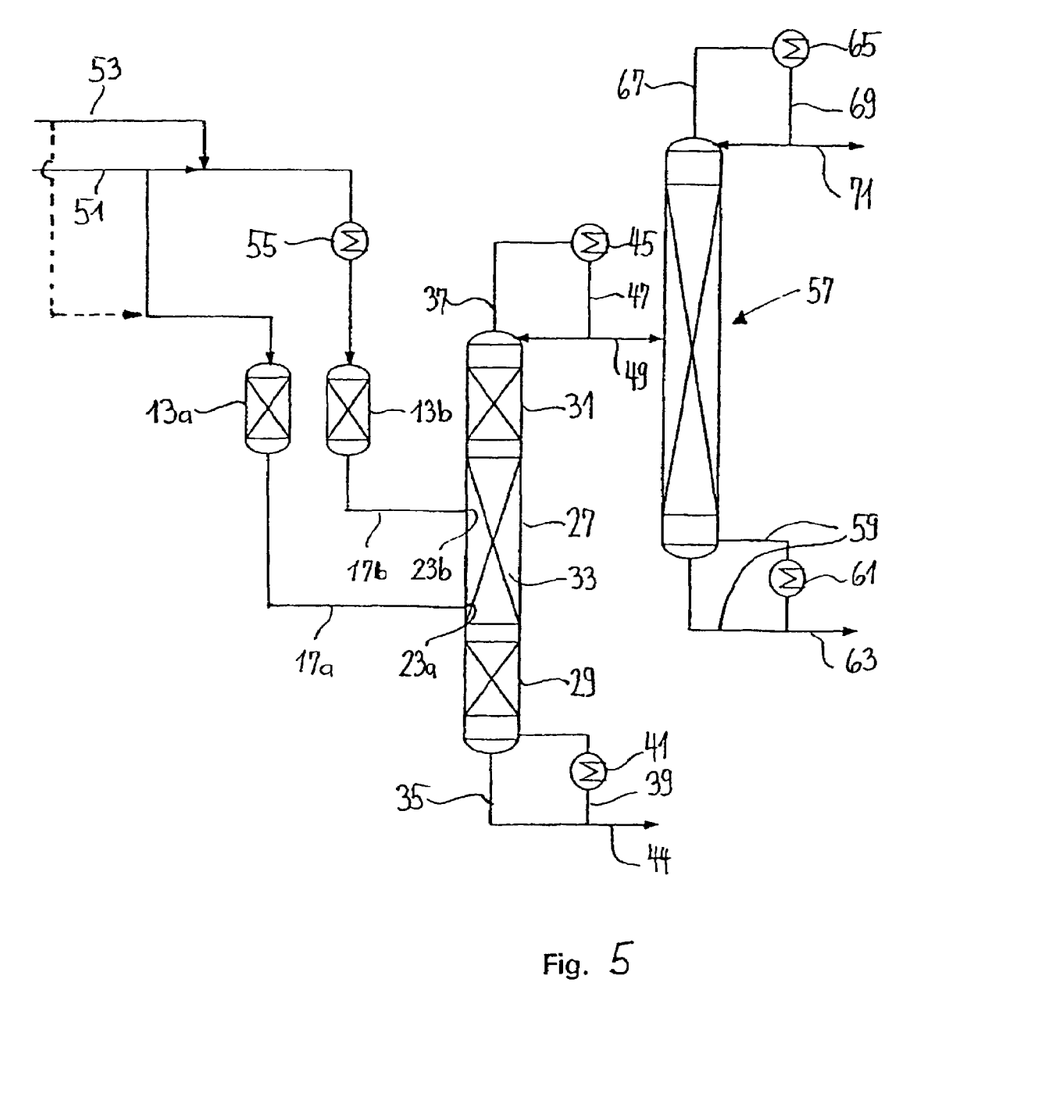
FIG. 5 diagrammatically shows a fifth embodiment of a device for the catalytic hydrolysis of carboxylates, with two pre-reactors, the feed from the pre-reactors being fed into the reactive distillation column at different points.

The illustrative embodiment in FIG. 5 differs from that in FIG. 4 in that the pre-reactors 13a and 13b are connected by means of separate lines 17a and 17b to the reactive distillation column 15. The line 17a is connected to an inlet 23a, and the line 17b to an inlet 23b. The inlet 23a is arranged in the region of the reaction zone or below the latter, and the inlet 23b in the region of the reaction zone or above the latter. The composition of the feed can be adjusted individually for each pre-reactor. The reaction conversion and the productivity can thereby be improved. In the case of using pure components, i.e. only water or only carboxylate, the use of a second pre-reactor may also be omitted.

The hydrolysis of a carboxylate will be described below with reference to the hydrolysis of methyl acetate as an example of other carboxylates. Methyl acetate flow having a proportion by weight of at least 50% methyl acetate is mixed with an amount of water at least equimolar with respect to methyl acetate, preferably a 4 to 7 times molar excess of water. The mixture is then heated by the heat exchanger 55, preferably to a temperature between 30 and 100° C., preferably 50 and 80° C., and fed into the preferably vertically arranged pre-reactor 13.

The pre-reactor 13 is packed with an acid solid-state catalyst, e.g. a cationic ion exchanger. The catalyst preferably has a particle size between approximately 0.35 to 3 mm. Such a catalyst material is available, for example, under the name Amberlyst 15 from the company Rohm and Haas. Alternative catalysts are, for example, zeolites, aluminium oxide, silicon oxide etc.

The methyl acetate/water mixture flows through the pre-reactor 13 in cocurrent from top to bottom, and comes into contact with the catalyst material during this. In this case, partial hydrolysis of the methyl acetate takes place. The conversion of the methyl acetate in the pre-reactor is between 20 and 100%, preferably between 50 and 80%, of the equilibrium conversion. The resulting reaction mixture is introduced via the line 17 into the catalyst zone 27 of the reactive distillation column 15, although the introduction may also take place above or below the catalyst zone. As a variant, part of the reaction mixture may be recycled back to the pre-reactor 15 (FIG. 3).

The reactive distillation column 15 is preferably operated in such a way that the more volatile methyl acetate rises in the catalyst zone, and the less volatile water flows down over the catalyst as reflux. In this case, intense contact between catalyst material, water and methyl acetate takes place, in the course of which methyl acetate is cleaved into acetic acid and methanol.

Depending on the desired purity and/or composition of the acetic acid, the reactive distillation column may be operated in such a way that unreacted water collects together with the acetic acid in the base of the column (case 1) or is essentially contained in the head flow of the reactive distillation column (case 2). In the first case, an acetic acid/water/methanol mixture is produced, which can be further separated e.g. by a downstream separation stage (FIG. 2). In the second case, aqueous or essentially anhydrous acetic acid with a purity >99% can be obtained.

The temperature of the pre-reactor, or of the reactive distillation column, respectively, may be established as a function of pressure, a certain overpressure making it possible to operate at a higher temperature.

In the process utilising the device in FIG. 2, the head flow of the reactive distillation column contains methyl acetate, methanol, water and low-boiling components. The base, which contains methanol, water, acetic acid and traces of methyl acetate, is removed as a so-called base flow. The volume ratio between the head flow 37 and the base flow 35 varies between 1:1 and 1:1000, preferably 1:30 to 1:200. The reflux ratio of the reactive distillation column is between 1 and 300, and preferably between 80 and 200. The base flow 35 of the reactive distillation column can be further separated in the distillation column 57. The head flow of the distillation column 57, exiting through the line 67, contains methanol and traces of methyl acetate, and the base flow (line 59) consists essentially of aqueous acetic acid.

In the process utilising the device in FIG. 3, the head flow of the reactive distillation column 15 contains methyl acetate, methanol, water and low-boiling components. The base flow contains either pure acetic acid, i.e. acetic acid at more than 99% proportion by weight, or aqueous acetic acid. The volume ratio between the base flow 35 and the head flow 37 preferably varies between 1:1 and 1:10, and more particularly preferably between 1:1 to 1:4. The reflux ratio of the reactive distillation column is between 1 and 100, and preferably between 5 and 50. The head flow of the reactive distillation column can be further separated in the distillation column 57. The head flow of the distillation column 57, exiting through the line 67, contains methanol, methyl acetate, water and low-boiling components. The base flow (line 59) contains essentially water.

EXAMPLES

In the following experimental examples, a cationic solid-state catalyst from the company Rohm and Haas, Germany was used (Amberlyst CSP 2). In the reaction distillation column, the catalyst was introduced into structured catalyst cracking.

1st Experiment (Prior Art)

A single reactive distillation column was used. The base flow contained a mixture of methyl acetate, methanol, acetic acid and water, which was separated in an additional purification column into a methyl acetate/methanol mixture and an acetic acid/water mixture.

The methyl acetate flow to be hydrolysed had the following composition (in percent by weight):

| The methyl acetate flow to be hydrolysed had the following composition (in per cent by weight): | |
|---|---|
| acetaldehyde: | 0.4% |
| methyl acetate: | 98.3% |
| methanol: | 1.3% |
| Reactive Distillation Column: | |
| inner diameter: | 220 mm |
| rectification zone: | 7 theoretical stages (TS) |
| reaction zone: | 6 TS |
| stripping zone: | 8 TS |
| Feed Flows: | |
| methyl acetate: | 35.87 kg/h |
| water: | 62.33 kg/h |
| Product Flows: | |
| head flow: | 0.67 kg/h |
| base flow: | 97.87 kg/h |
| Experimental Conditions: | |
| head pressure: | 956 mbar |
| feed point: | 13 TS |
| reflux ratio: | 220 |
| heat exchanger temperature: | 73.7° C. |
| Result: | |
| methyl acetate conversion: | 79.2% |
| composition base flow of the reactive distillation column in per cent by weight: | |
| methyl acetate: | 6.97% |
| methanol: | 14.19% |
| water: | 56.61% |
| acetic acid: | 22.24% |

2nd Experiment: Combination of Pre-Reactor with Reactive Distillation Column

A combination of pre-reactor with reactive distillation column was used. The base flow of the reactive distillation column contains methanol, acetic acid, water and traces of methyl acetate. This mixture was separated in a distillation column into a methanol flow containing traces of methyl acetate and an acetic acid/water mixture.

| The methyl acetate flow to be hydrolysed had the following composition (in per cent by weight): | |
|---|---|
| acetaldehyde: | 0.001% |
| methyl acetate: | 96.53% |
| methanol: | 3.46% |
| Reactive Distillation Column: | |
| inner diameter: | 220 mm |
| rectification zone: | 7 theoretical stages (TS) |
| reaction zone: | 6 TS |
| stripping zone: | 8 TS |
| Feed Flows: | |
| methyl acetate: | 38.61 kg/h |
| water: | 58.20 kg/h |
| Product Flows: | |
| head flow: | 1.0 kg/h |
| base flow: | 92.92 kg/h |
| Experimental Conditions: | |
| head pressure: | 967 mbar |
| feed point: | 13 TS |
| reflux ratio: | 122 |
| heat exchanger temperature: | 83.7° C. |
| Result: | |
| methyl acetate conversion: | 57.6% |
| after pre-reactor: | |
| overall: | 98.0% |
| composition base flow of the reactive distillation column in per cent by weight: | |
| methyl acetate: | 0.01% |
| methanol: | 18.93% |
| water: | 50.54% |
| acetic acid: | 30.68% |

Example 3

Simulation of the hydrolysis and separation reaction by means of the simulation program PRO/II of the company SIMSCI (Simulation Sciences Inc.) with the aim of obtaining pure acetic acid from a methyl acetate flow utilising a pre-reactor/reactive distillation column combination according to the invention:

| Reactive Distillation Column: | |
|---|---|
| rectification zone: | 10 theoretical stages (TS) |
| reaction zone: | 25 TS |
| stripping zone: | 15 TS |
| For the methyl acetate flow to be hydrolysed, the following composition was assumed (in per cent by weight): | |
| acetaldehyde: | 0.9% |
| methyl acetate: | 93.1% |
| methanol: | 2.1% |
| water: | 3.9% |
| Feed Flows (in kg/h): | |
| feed flow: | 6500 kg/h (of acetaldehyde, MeAc, MeON and H$_2$O) |
| water: | 7100 kg/h |
| Product Flows (in kg/h): | |
| head flow: | 10,000 kg/h |
| base flow: | 3600 kg/h |

| -continued | |
|---|---|
| Experimental Conditions: | |
| head pressure: 1.5 bar | |
| feed point: | 35 TS |
| reflux ratio: | 10 |
| heat exchanger temperature: | 120° C. |
| Result: | |
| methyl acetate conversion: | 57.6% |
| after prereactor: | |
| overall: | 73.3% |
| base flow composition of the reactive distillation column in per cent by weight: | |
| methyl acetate: | 0.00% |
| methanol: | 0.00% |
| water: | 0.01% |
| acetic acid: | 99.9% |

The process according to the invention is suitable, in particular, for the hydrolysis of low molecular weight esters (esters with C1 to C4 or higher alcohols), e.g. methyl acetate, methyl formate and allyl acetate.

Allyl alcohol can inter alia be produced by the hydrolysis of allyl acetate. The hydrolysis is in this case carried out according to known conventional methods in the presence of mineral acids or ion exchangers as catalyst.

The production of formic acid likewise takes place by a hydrolysis reaction. In this case, methyl formate is reacted with excess water to give formic acid and methanol. The reaction can in this case be carried out autocatalysed by formic acid (DE-A-44 449 79) or in the presence of acid catalyst, e.g. ion exchanger (DE-A-42 373 39). The processing of the hydrolysis products conventionally takes place with separation methods such as distillation, extraction, etc.

| Legend | |
|---|---|
| 11 | hydrolysis device |
| 13 | pre-reactor |
| 15 | reactive distillation column |
| 17 | connecting line |
| 19 | pre-reactor inlet |
| 21 | pre-reactor (13) outlet |
| 23 | R.D. column inlet |
| 25 | catalyst bed |
| 27 | catalyst zone |
| 29 | lower rectification zone |
| 31 | upper rectification zone |
| 33 | solid-state catalyst |
| 35 | R.C foot line |
| 37 | R.C. head line |
| 39 | line between line 35 and heat exchanger |
| 41 | column foot heat exchanger |
| 43 | line between heat exchanger and column foot |
| 45 | branch line |
| 47 | recycling line |
| 49 | line |
| 51 | feed line for carboxylate |
| 53 | water |
| 55 | heat exchanger before the pre-reactor (13) |
| 57 | distillation column |
| 59 | circulation line |
| 61 | heat exchanger for base of the distillation column |
| 63 | branch line |
| 65 | condenser |
| 67 | line between distillation column and condenser |
| 69 | line between condenser and distillation column |
| 71 | line for the removal of the distillate |

The invention claimed is:

1. Process for hydrolytically obtaining a carboxylic acid and alcohol from a corresponding carboxylate and water, the process comprising:
   feeding a flow containing carboxylate to a pre-reactor, in which the carboxylate is brought into contact with a first catalyst in the presence of water, such that the carboxylate is partially cleaved into hydrolysis products; and
   drawing off the reaction mixture from the pre-reactor and at least partially feeding the reaction mixture into a reactive distillation column, and bringing the reaction mixture into contact with a second hydrolysis catalyst for at least partial conversion of remaining carboxylate into carboxylic acid and alcohol, a resulting reaction mixture being simultaneously separated at least partially into components in the reactive distillation column, more volatile compounds, including alcohol, being drawn off from a head of the reactive distillation column as a head flow and less volatile compounds, including carboxylic acid, collecting at least partially in a base of the column as a bottom fraction, which can be drawn off as a base flow.

2. Process according to claim 1, wherein at least one of the head flow of the reactive distillation column or the base flow is delivered to at least one further separation stage, and is at least partially separated into the components.

3. Process according to claim 1, wherein the carboxylate is mixed with at least an equi-molar amount of water, and the mixture of carboxylate and water is fed into the pre-reactor.

4. Process according to claim 1, wherein a molar ratio of carboxylate and water is between approximately 1:1 and 1:15.

5. Process according to claim 4, wherein the molar ratio is between 1:2 and 1:10.

6. Process according to claim 4, wherein the molar ratio is between 1:4 and 1:7.

7. Process according to claim 4, wherein the molar ratio is between 1:3 and 1:5.

8. Process according to claim 1, wherein the mixture of carboxylate and water is heated to a temperature of between 30 and 100° C.

9. Process according to claim 8, wherein the temperature is between 40° and 90° C.

10. Process according to claim 8, wherein the temperature is between 50° and 80° C.

11. Process according to claim 1, wherein the reaction mixture from the pre-reactor is fed into the reactive distillation column in a region where the catalyst is arranged.

12. Process according to claim 1, wherein the reactive distillation column is operated such that unreacted water and the more volatile compounds are essentially contained in the head flow.

13. Process according to claim 12, wherein the reaction mixture from the pre-reactor is fed into the reactive distillation column at a point below a catalyst zone center or below a catalyst zone.

14. Process according to claim 12, wherein the head flow is delivered to a further separation stage configured as a distillation or extraction column, in which the mixture is further separated.

15. Process according to claim 1, wherein the reactive distillation column is operated such that the carboxylic acid and unreacted water remain in the base of the reactive distillation column.

16. Process according to claim 15, wherein the reaction mixture from the pre-reactor is fed into the reactive distillation column at a point above a catalyst zone center or above a catalyst zone.

17. Process according to claim 15, wherein the base flow of the reactive distillation column is delivered to a further separation stage configured as a distillation or extraction column, in which the mixture is further separated.

18. Process according to claim 1, wherein the head flow and the base flow of the reactive distillation column are delivered to a further separation stage configured as one distillation or extraction column for each of the head flow and the base flow, in which the respective mixture is further separated.

19. Process according to claim 1, wherein the process is operated continuously, such that the carboxylate and the water or a mixture thereof, respectively, are continuously fed into the pre-reactor, and the resulting reaction mixture is drawn off continuously from the pre-reactor and fed into the reactive distillation column, where unreacted carboxylate is for the most part converted into hydrolysis products thereof, the hydrolysis products being drawn off continuously as a head flow or as a base flow, and optionally delivered to a further separation stage.

20. Process according to claim 1, wherein the carboxylate is a methyl, ethyl, i- or n-propyl ester, i- or n-butyl ester, acetates thereof, or a mixture of these ester compounds.

21. Process according to claim 1, wherein the hydrolytic obtaining of a carboxylic acid and alcohol is performed using a hydrolysis and separation device having at least one said reactive distillation column for converting the carboxylate into the carboxylic acid and the alcohol and at least partial separation of the hydrolysis products into individual components, the device comprising:
   at least one said pre-reactor having at least one inlet and one outlet for respectively supplying and discharging a fluid flow comprising the carboxylate into the pre-reactor and therefrom, respectively;
   the first catalyst arranged or deposited in the pre-reactor;
   first heating means for heating the fluid flow or the pre-reactor;
   the reactive distillation column having an inlet, which is connected by a connecting line to the outlet of the pre-reactor, the reactive distillation column comprising:
   a catalyst zone comprising the second catalyst and at least one rectification zone, which is formed by at least one of distillation packing, Raschig rings, and separating stages;
   lines, connected respectively to the distillation column head and the distillation column base, for drawing off the head flow and the base flow, respectively; and
   second heating means for heating the base of the reactive distillation column.

22. Process according to claim 21, wherein the pre-reactor is arranged approximately vertically, (i) the inlet being arranged at a top of the pre-reactor and the outlet at a bottom of the pre-reactor or (ii) the outlet being arranged at the top of the pre-reactor and the inlet at the bottom of the pre-reactor.

23. Process according to claim 21 wherein, two pre-reactors or one pre-reactor having two reaction chambers are used, and the device comprises means to feed the fluid flow respectively through one of the pre-reactors or one of the reaction chambers, so that the other pre-reactor or the other reaction chamber, respectively, can be provided with fresh catalyst.

24. Process according to claim 21, wherein the reactive distillation column has a catalyst zone and one lower and one upper rectification zone, respectively, the upper rectification zone being arranged above the catalyst zone and the lower rectification zone being arranged below the catalyst zone.

25. Process according to claim 24, wherein the inlet of the reactive distillation column is located in a region of the catalyst zone.

26. Process according to claim 21, wherein the pre-reactor is tubular, and the first catalyst is a bed of a solid catalyst.

27. Process according to claim 21, wherein at least the second catalyst is formed as structured catalyst packing.

28. Process according to claim 27, wherein the structured catalyst packing is formed by packing elements having cavities, a catalyst material being disposed in the cavities.

29. Process according to claim 21, wherein the first and second catalysts are acid solid-state catalysts, the first catalyst having a particle size of between approximately 0.35 and 3 mm and the second catalyst having a particle size of between approximately 0.5 and 1.5 mm.

30. Process according to claim 29, wherein the second catalyst has a particle size of between approximately 0.63 and 1 mm.

31. Process according to claim 29, wherein the second catalyst has a particle size of between approximately 0.7 and 1 mm.

* * * * *